United States Patent [19]

McLaughlin

[11] 4,096,860

[45] Jun. 27, 1978

[54] DUAL FLOW ENCATHETER

[76] Inventor: William F. McLaughlin, 67 Balboa Cove, Huntington Beach, Calif. 92663

[21] Appl. No.: 620,600

[22] Filed: Oct. 8, 1975

[51] Int. Cl.² .................................................. A61M 5/00
[52] U.S. Cl. ..................................... 128/214.4; 128/221
[58] Field of Search ....................... 128/214.4, 221, 347, 128/348, DIG. 16

[56] References Cited

U.S. PATENT DOCUMENTS

| 3,585,996 | 6/1971 | Reynolds et al. | 128/214.4 |
|---|---|---|---|
| 3,610,226 | 10/1971 | Albisser | 128/2 F |
| 3,670,729 | 6/1972 | Bennett et al. | 128/214.4 |
| 3,739,778 | 6/1973 | Monestere et al. | 128/214.4 |
| 3,757,771 | 9/1973 | Ruegg et al. | 128/214.4 |
| 3,766,916 | 10/1973 | Moorehead et al. | 128/214.4 |
| 3,875,938 | 4/1975 | Mellor | 128/214.4 |
| 3,895,632 | 7/1975 | Plowiecki | 128/214.4 |
| 3,903,885 | 9/1975 | Fuchs | 128/214.4 |
| 3,983,864 | 10/1976 | Sielaff et al. | 128/214.4 X |
| 4,000,739 | 1/1977 | Stevens | 128/214.4 |
| 4,014,333 | 3/1977 | McIntyre | 128/214.4 |
| 4,016,879 | 4/1977 | Mellor | 128/214.4 |

FOREIGN PATENT DOCUMENTS

| 2,139,004 | 2/1973 | Germany | 128/214.4 |

OTHER PUBLICATIONS

Piazza et al. - Trans. Amer. Soc. Artific. Inter. Orgs., vol. X, Apr. 1964, pp. 136–138.

Primary Examiner—Dalton L. Truluck
Attorney, Agent, or Firm—Spensley, Horn & Lubitz

[57] ABSTRACT

The following specification discloses an encatheter adapted for biaxial flow for receipt of a syringe at one end with a main axial passage interconnecting a plastic or teflon insertion conduit at the other end adapted for placement in a blood vessel with a needle. The hub in its main axial passage, has a flapper or one way control valve, that can be made of an elastomeric material. The valve is adapted for receiving the needle therethrough for simultaneous insertion of the insertion conduit and the needle within the interior of a blood vessel. The insertion conduit remains within the blood vessel after the needle is removed, at which time a second interior tube is implaced within the insertion conduit through the main axial passage and valve to provide coaxial orientation between the two. Th conduit and tube each respectively connect to a biaxial flow device for branched flow through the device to two rubber tubes. The first tube connected to the conduit allows body fluid to flow to an exterior device for processing, such as a hemodialysis machine, while the second tube returns to the coaxial tube for flow back to the blood vessel after processing the body fluid.

10 Claims, 10 Drawing Figures

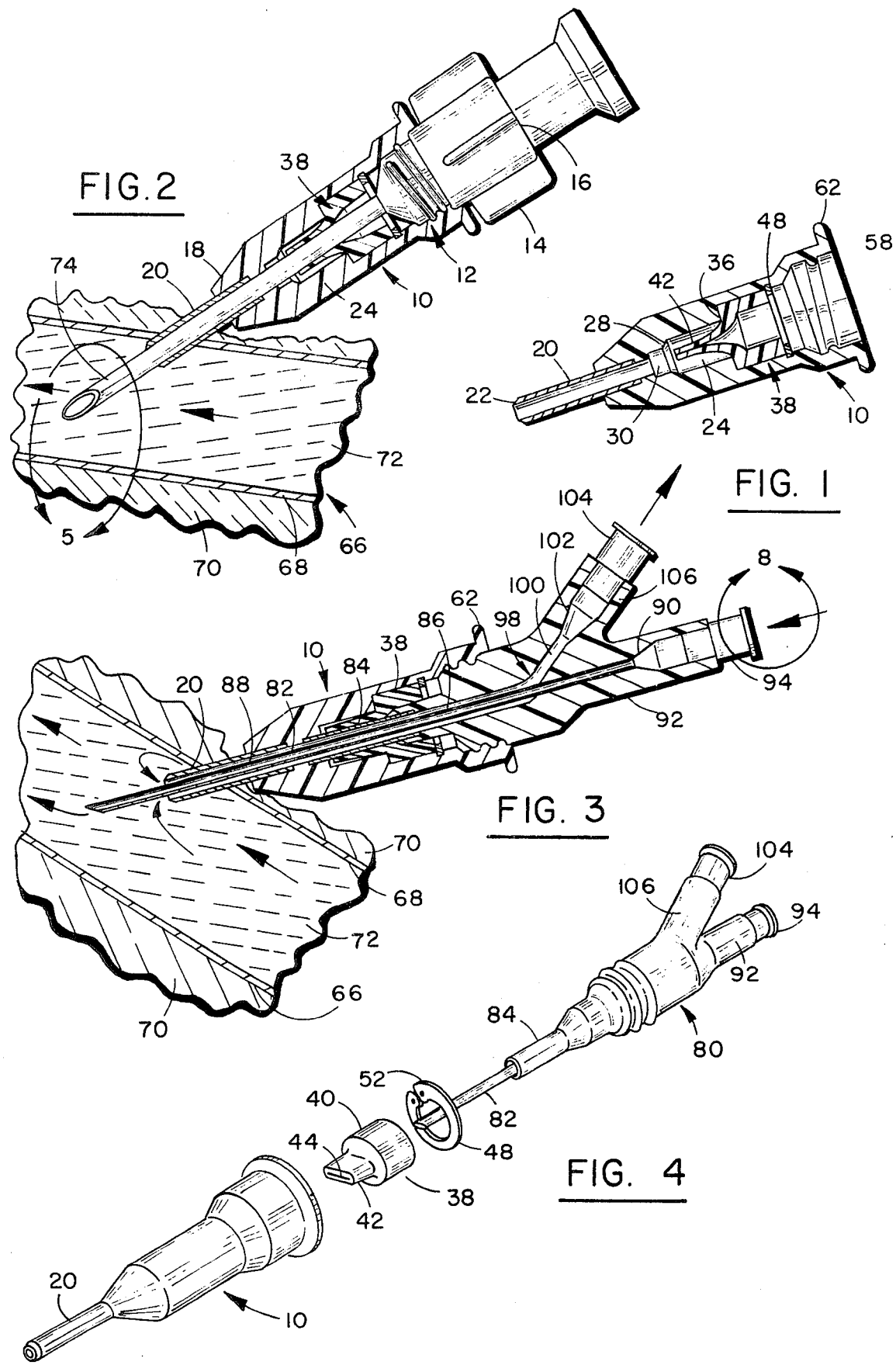

DUAL FLOW ENCATHETER

BACKGROUND OF THE INVENTION

1. Field of the Invention

This invention resides within the art related to withdrawing or implacing a fluid within a member, such as a blood vessel, or other portion of the body. More specifically, it is directed toward the problem of hemodialysis wherein blood is withdrawn from a blood vessel, cleansed through a dialysis process, and returned to a blood vessel.

2. The Prior Art

The prior art related to the insertion of needles for the withdrawal or implacement of fluid in a blood vessel, generally relates to the placement of a single needle for both functions. Oftentimes it is necessary to withdraw or implace blood within a blood vessel for various medical functions, such as during certain operations and the general transfusion or giving of blood.

Lately, it has been common to withdraw blood for purposes of hemodialysis. In particular, hemodialysis has become an important function in the maintenance and preservation of human life when a person has lost substantial or total use of his kidneys. In other words, hemodialysis techniques allow one to be fluid mechanically linked to a dialysis machine, so that blood flowing through the individual is withdrawn and cleansed, after which it is returned to the body. During the withdrawal and return of the blood through a blood vessel in the human body, it has been common to use two needles in separate vessels. Also, a fistula, or surgical connection between a vein and an artery is used to provide positive flow, while at the same time allowing return of the blood.

As can be understood, in the withdrawal of blood by a needle, it is first of all necessary to puncture the blood vessel. During the puncture of a blood vessel, a certain amount of tissue is removed by virtue of the sharp leading edge of the needle going through the blood vessel wall and removing a portion of the tissue. In effect, it cuts a hole in the area within the interior of the needle. This is undesirable and certain attempts have been made by having a pointed needle with a lateral entrance so that the tissue is effectively spread to allow insertion of the needle rather than a cutting of the vessel wall.

More importantly, the insertion of a needle in hemodialysis processes is one wherein it must be inserted periodically over long periods of time, and in approximately the same general location. This causes attendant scarring and damage to the vessel wall, consequently lowering the chronological viability of the vessel. Furthermore, repeated damage to the vessel can also cause clot formation. As can be understood, clots are dangerous to a person's general health by virtue of the fact that oftentimes aglomerations of clots build up, creating a hazard to one's cardiovascular and pulmonary systems.

The problem becomes substantially exaggerated when hemodialysis is the reason for inserting a needle within a person's blood vessels. In particular, the prior art teachings rely substantially upon the utilization of two needles, or one needle with a mechanical alternator. In the former, one needle is used for withdrawal of blood from a blood vessel, while the other needle is used for replacement of the cleansed blood after it passes through the dialysis process. The attendant utilization of two needles within a blood vessel has created a situation wherein the danger due to clots is increased two-fold, as well a doubling the damage done to the blood vessel, thereby lowering the long term viability of the vessel.

This invention seeks to overcome the foregoing deficiencies of the prior art. In particular, it is the thought of the inventor that biaxial flow through one needle of limited size for hemodialysis and the removal and replacement of the blood in other medical procedures is particularly desirable. As a consequence, the inventor has developed a process and device hereof which removes many of the attendant problems of the prior art.

In particular, the invention hereof incorporates a hub for use with a syringe having an axial cavity and passage therein with an elastomeric valve. The valve is a one way flow valve and allows the implacement of a needle or conduit therethrough. The valve is interconnected through the axial passage to the end of the hub opening to an extending conduit therein. The conduit is of a size capable of receiving a needle in coaxial adjacent interior relationship.

The needle with the extension conduit surrounding it in part along its axis, is inserted into a blood vessel with the conduit also being inserted therein. The conduit serves to stretch the opening initially formed by the needle. Upon insertion of the needle, flow is allowed to be transmitted through the needle to a syringe in connected relationship thereto. The flow into the syringe indicates that a positive placement of the needle and the extension conduit of the hub has been effectuated. After insertion, the needle can be withdrawn axially through the extension conduit and the valve to provide withdrawal thereof and at the same time closure of the axial passage connecting the conduit. A second biaxial flow device having coaxial conduits in the form of an interior tube and an exterior main conduit can be inserted into the hub downwardly through the extension conduit into the blood vessel. In other words, the biaxial flow device comprising the coaxial tube and main conduit is implaced into the already inserted extension conduit and hub of this invention through the valve which prevents flow from the blood vessel between procedures.

Flow through the outer main conduit is branched away to allow flow to whatever receiving or processing apparatus is desired. In one particular case of the example hereof, flow is allowed to be transmitted to a hemodialysis machine. The hemodialysis machine then cleanses the blood and allows it to flow to the interior tube of the biaxial flow device and back to the blood vessel.

The invention also overcomes the deficiencies of the prior art by allowing a stepped enlargement of the opening of a blood vessel to avoid tearing and rupture of the side walls. Thus, an attendant stretching and insertion of the needle takes place without substantial damage to the blood vessel and side wall thereof.

As will be seen from the following specification and claims hereof, this invention overcomes the deficiencies of the prior art and should be read broadly in light of the general biaxial flow process and device for effectuating the same specified and claimed therein.

SUMMARY OF THE INVENTION

In summation, this invention comprises a biaxial flow device for insertion of the device within a blood vessel, and withdrawing and replacing fluid therefrom on a simultaneous basis.

More particularly, the invention comprises a simultaneous flow device incorporating a hub with an extension conduit and a valve therein for receipt of a needle therethrough. The extension conduit is of sufficient size to allow the passage of the needle therethrough adjacent the interior side walls thereof with an attendant extension thereof from its opening. The needle with the extended conduit is adapted for combined insertion within a blood vessel, after which it can be withdrawn while the valve prevents the back flow of blood through the axial passage of the hub.

A biaxial flow device can then be inserted within the hub and through the conduit to allow for the withdrawal of fluid and the simultaneous replacement thereof. The biaxial flow device comprises a branched member with a main conduit for passage through the valve and to provide interconnection to the extending conduit in the blood vessel.

The biaxial flow device has a coaxial inner passage or tube which allows for the flow from the apparatus that is receiving the fluid back into the blood vessel.

In effect, the outer main conduit of the device allows for the flow of fluid from a blood vessel to a hemodialysis machine after which the blood is cleansed. The flow then returns to the inner tube at a branch of the biaxial flow device, after which it flows back to the blood vessel, thereby allowing dialysis during an extended period of time through a single opening of a blood vessel.

As a consequence of the foregoing, this invention and its attendant embodiments and teachings as claimed should be read broadly in light of the prior art to cover fluid flow through a single opening in a blood vessel for coaxially receiving, transmitting, and returning such flow.

BRIEF DESCRIPTION OF THE DRAWINGS

The invention will be more clearly understood by reference to the description below taken in conjunction with the accompanying drawings wherein:

FIG. 1 shows a cross sectional view of the insertion hub with the conduit extension that is received with a blood vessel;

FIG. 2 shows a sectional view of the hub of FIG. 1 inserted within a blood vessel with a needle;

FIG. 3 shows the hub of FIG. 1 with the needle of FIG. 2 removed and the biaxial flow device of this invention inserted therein;

FIG. 4 shows an exploded view of the biaxial flow device and the hub shown in FIG. 3;

DESCRIPTION OF THE PREFERRED EMBODIMENTS

THE APPARATUS

Figure 5:
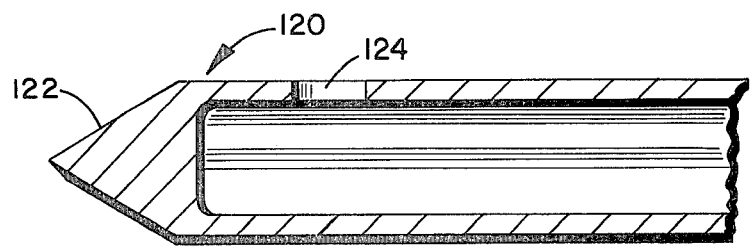
FIG. 5 shows an alternative embodiment of a needle in cross section that can replace the needle shown in Circle 5 of FIG. 2.

Looking at FIGS. 1 through 4, a hub 10 is shown which incorporates some of the operative characteristics of this device. The hub 10 is of the type that can receive a syringe fitting at a connector generally shown as connection 12. The connection 12 is of a type commercially referred to as a Luer-Lok, a registered trademark. The Luer-Lok 12 is in effect a quick twist type of connection. However, connection 12 can be in any suitable form, such as a frictional engagement, a twist device, or bayonet connection. The intent is that a connection can be made at connection 12 between the hub 10 of this device and a syringe.

To this end, a fitting 14 is shown that can receive a syringe at end 16 which is open. The syringe fitted at end 16 can be of any particular type, so long as it can withdraw a quantity of blood, or be utilized as a general means for inserting the hub 10 of this invention.

Looking more particularly at the hub 10 of this invention, it can be seen that it tapers downwardly at its end 18 and has an conduit 20 extending therefrom. The extending conduit 20 is received within the tapered end 18 of the hub and can be sealed by any suitable means such as heatsetting or by an adhesive. Furthermore, the hub 10 and the extended conduit 20 can be formed as one continuous body. The extending conduit 20 has a tapered end 22 thereof which has been chamfered to allow for insertion within the blood vessel in the manner to be described.

Looking more particularly at the hub 10, and the extension conduit 20, it can be seen that a cavity 24 therein extends in connected relationship to the conduit 20 to provide for a coaxial passage therethrough. The conduit 20 can be formed of any suitable plastic material, however, in this particular case, it has been formed of teflon and has been provided with a barium or bismuth impregnation, so that it can be detected by XRay after it has been inserted within a blood vessel.

The hub 10 with the cavity 24 thereof has a terminal tapered chamfered surface 28 which leads into a receipt opening or connection port 30 from the cavity 24. The cavity 24 in conjunction with the tapered surface 28 and opening 30 provides a suitable receipt area for a portion of the biaxial flow device in a manner to be described.

The cavity 24 has been stepped at surface 36 to provide for receipt and maintenance of a valve member 38. The valve member 38 comprises a circular or cylindrical walled portion 40 tapering down to a nipple-like element 42 having a slit 44 therethrough. The slit 44 is generally in a closed condition, so as to provide for an elastomeric valving in the form of a one way valve so that flow can only take place when it has been separated by a tubular member passing therethrough, or by positive pressure from the righthand side of the drawings. Any flow backwardly from the lefthand side of the drawings to the right, is shut off by the slit 44 of the valve member.

The valve member 38 is secured within the cavity 24 and against the shoulder 36 by means of an expansion ring 48. The expansion ring 48 is typical of most expansion rings, and is seated within an interior groove of the hub 10 that has been provided around the interior surface of the cavity 24. The expansion ring 48 has two openings which allow for a squeezing of the expansion ring into a gap 52 thereof so that it can be removed from the circular groove into which the expansion ring 48 expands within the cavity 24 of the hub 10.

As has been previously stated, the connecting portion of the hub 10 has a series of threadlike members 12 which circumscribe the interior portion to provide a quick threaded connection known in the industry as a Luer-Lok. This allows a syringe connection to be threaded in the mating threads. An outer circumferential flange 62 is shown for ease of entrance of the syringe.

Looking more particularly at FIGS. 3 and 4, the hub 10 is shown with its extension member having been implaced in a blood vessel 66, having walls 68 and tissue 70 surrounding it. The flow through the blood vessel is shown in the form of fluid 72 passing therethrough. The flow of fluid 72 is to be extracted and replaced in the blood vessel 66 in the manner to be described. The hub 10 has been implaced within the blood vessel 66 so as to allow the extension conduit or insertion conduit 20 to be implaced within the opening previously provided by a needle 74. The needle 74 which is attached to the syringe along with the extension conduit 20 has been inserted within the blood vessel 66.

In the showing of FIG. 3, the needle 74 has been removed. In this particular case, the removal has been accommodated by previously allowing the flow of blood or fluid into the syringe connected to the syringe connection end 16, to ascertain positive flow and placement. After positive blood flow is ascertained, or a sample taken, the needle 74 can be removed along with the attendant syringe. The valve 38 can then respond to curtail further flow through the slit 44, and the cavity 24.

With the extension conduit still within the sidewall 68 of the blood vessel 66, the biaxial flow device of this invention 80 is inserted into the hub 10. Upon insertion into the hub 10, it proceeds through the valve 38 and the slit 44 thereof to then pass through the extension conduit 20, thence into the blood vessel 66. The biaxial flow device extends outwardly from the end of the extension conduit 20 sufficiently to provide biaxial flow.

The biaxial flow device 80 of this invention comprises a metallic tube 82 within a main conduit 84. The metallic tube 82 within the main conduit 84 allows for the biaxial flow in a space 86 provided by the outer walls of the metal tube and the inner walls of the main conduit 84. Thus, flow is provided within a space 88 of the metal tube 82 and the space 86 between the main conduit 84 and the metal tube 82. The main conduit 84 is designed to rest at its terminal end against a shoulder of the receipt space 30. Thus, continuous flow to the space 86 or lumen, as it is referred to in the art, is continuous without substantial interruptions of the flow or tortuous paths which are deleterious to the blood platelets.

One of the objects of transmitting blood in any device is to avoid tortuous paths, constrictions, and general conformations that damage the blood. Thus, the shoulder provided within the opening 30 is designed to have an inside diameter equivalent to the inside diameter of the main conduit 84. This accommodates flow through the lumen, space, or passage 86 in a continuous non-tortuous manner to prevent blood damage.

The metal tube 82 terminates at a tapered opening 90 which connects into a tube receipt opening within a branch 92 of the biaxial flow device 80 of this invention. The branch 92 with the opening therein receives approximately a quarter inch tube 94 which allows flow therefrom into the metal tube 82.

The flow within the space 86 between the outer walls of the metal tube 82 and the main conduit 84 makes a junction at the branch 98 which flows into the conduit 100 of the biaxial flow device 80 of this invention formed within a branch 106. The passage 100 spreads outwardly at a flared portion 102 where it meets a second quarter inch tube 104 for the flow of fluid from the branch 106 of the biaxial flow device 80 into the tube.

As can be seen, the tube 104 mates within an opening of a branch 106. The branch 106 is designed so that a minimum amount of disturbance is provided to the blood flowing through the opening 100 thereof.

The biaxial flow device 80 is such that it allows for continued removal of blood from the blood vessel 66, the subsequent processing thereof in whatever manner desired, such as oxygenation, and more importantly, in this particular embodiment, hemodialysis. Afterwards, the blood is returned via the metal tube 82 extending from the extension or insertion conduit 20.

In effect, the flow of fluid 72 passes through the blood vessel into the opening provided by the space 86 between the tube 82, and extension conduit 20, the main conduit 84, and the remainder of the path through the biaxial flow device. Afterwards, the blood flows into the tube 104 for dialysis or processing.

The blood is then delivered through the tube 94 back to the metal tube 82 for delivery into the blood vessel 66 in the direction of the arrow emanating therefrom. In this manner, continuous flow is provided through only one opening of the blood vessel 66.

Looking more particularly at the remaining portion of the disclosure, it can be seen in FIG. 5 that an alternative needle 120, analogous in function to needle 74, has been shown with a point 122. The point 122 does not render as much damage to the sidewalls 68 of the blood vessel 66 by virtue of the fact that it spreads the cellular structure rather than tearing a hole therethrough by the sharpened edges of the needle 74. After insertion, the needle 120 provides for flow through an opening 124 thereof, so that the positive flow of blood or other fluid can be determined by the syringe connected to syringe connection 16. In other words, the needle 120 of FIG. 5 is a substitute needle for needle 74, and is then removed prior to the insertion of the biaxial flow device 80 within the hub 10.

Figure 6:
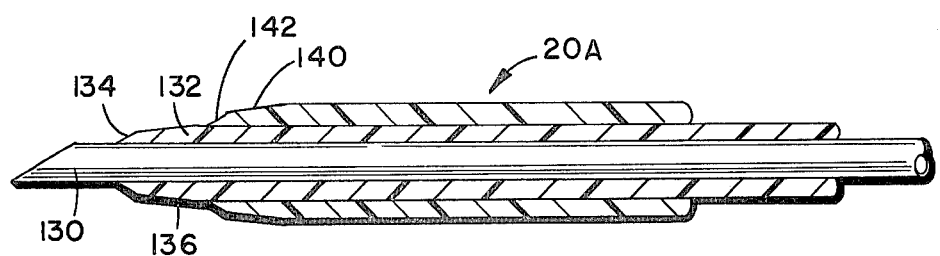
FIG. 6 shows a step-up form of needle in cross section having a substantially limited interior metal needle with a stepped-up secondary insertion stretching portion with an outer main extension conduit surrounding it.

Looking at FIG. 6, a needle 130 is shown having an opening that can be like the opening of needle 74 or for that matter, like the needle shown in FIG. 5. However, the needle has been circumferentially stepped by a teflon sleeve portion 132 having a chamfered end 134 which is in contact with the surrounding circumferential area of the needle. The chamfered surface 134 of the member 132 has a chamfer 134, as previously mentioned, and a taper 136 which terminates at a second chamfer 142 and tapered portion 140. The foregoing chamfer 142 and taper 140 can be a portion of the extension conduit 20 and shall be designated in this case, insertion conduit 20(A).

Thus, extension or insertion conduit 20(A) allows for a stepped insertion of the extension conduit 20(A) without substantial rupture of the walls 68 of the blood vessel 66. Instead of tearing the walls substantially by means of a needle and the extension conduit 20 which is to be inserted within the wall of the blood vessel 66, the taper and chamfers respectively from 134 through 142, allow spreading of the opening. Thus, less clotting is required in order to close an opening after the member 20(A) is withdrawn. This of course prevents the larger aglomeration of clots which are deleterious to a patient's health.

Figure 7:
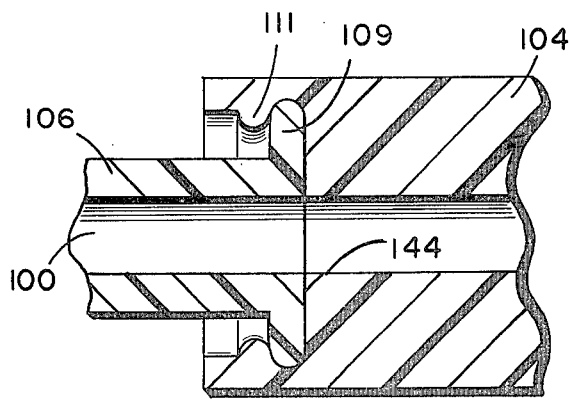
FIG. 7 shows a sectional view of an alternative connection means taken at the joinder of the hub of FIG. 3 and the biaxial flow device; and, FIG. 8 shows a plug arrangement which can be oriented at the ends of the tube shown in FIGS. 3 and 4 to prevent inadvertent flow therefrom.

A connector in FIG. 7 is shown in order to effectuate a smooth connection between the tubes 94 and 104 and the biaxial flow device 80. For example, the tube 104 has been connected to the branch 106 having circumferential flange 109 therearound. The circumferential flange 109 and inner circumferential shoulder or ridge 111 seals the interior of the opening within the tube 104. Also, a smooth opening between the space or lumen 100 and the tube 104 provides for smoothness at the interface 144.

Figure 8:
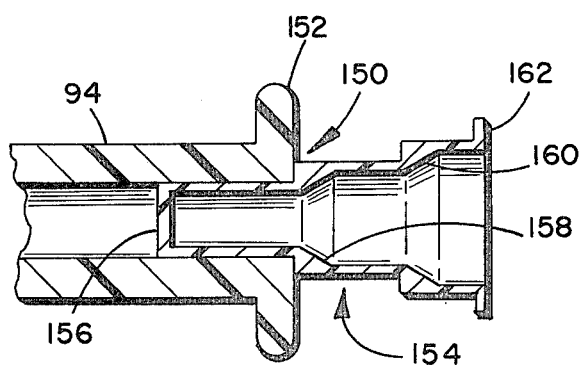

FIG. 8 interfaces with one of the tubes 94 or 104. The end 150 of the tube 94 has a circumferential flange or rim 152 thereof which can receive a plug 154 therein. The plug 154 has a stopper end 156 with an expanded stepped portion comprising two steps 158 and 160 with an end flange 162. The plug 154 can accommodate various sized openings of the tube 94 and 104 by virtue of its stepped relationship.

The reason for the plug 154 and attendant blockage is that upon insertion of the biaxial flow device 80 into the hub 10 allowing flow therethrough, inadvertence and human error might possibly allow continued flow through the tubes 104 and 94 if they are not properly plugged.

OPERATION OF THE DEVICE

In operation, the hub 10 with the needle 74 and the extension conduit 20 is inserted into the blood vessel 66. Upon insertion within the blood vessel 66, flow is permitted by virtue of the fact that the valve member 38 is open and the passage through the needle 74 allows for pressure from the blood vessel 66 to cause flow backwardly into the syringe. The syringe which has been connected to the syringe end connection 16 which can comprise a portion of the syringe, is then removed. It is removed by an easy twist at the threaded connection point 12.

Upon removal of the syringe and the needle 74, the extension conduit 20 remains in the side wall 68 of the blood vessel. The valve 38 by removal of the tube 82 then closes at its slit 44. Upon closure of the slit 44, flow is then stanched by the valve 38 being in the closed position.

With the extension conduit 20 still in the sidewall 68 of the blood vessel 66, the biaxial flow device 80 is axially passed and threaded into the hub 10. This causes the slit 44 of the valve 38 to open. Upon insertion, flow can then take place within the space 86 between the tube 82 and the main conduit 84. Thus, flow is then transmitted at the branch 98 to the tube 104 connected to a processing apparatus.

After the blood has been processed, such as by hemodialysis, it is then returned through the tube 94 and the metal tube 82 back into the blood vessel 66. This completes the circuit through the biaxial flow device 80.

The needle 74 can be of a smaller outside diameter than the inside diameter of the extension conduit 20, thereby creating a passage between the two. The passage can be valved by the valve member 38 or the needle 74 sealed to prevent flow therearound from the passage. The passage between the needle 74 and the conduit in such a case can terminate in the cavity 24 surrounding the valve 38 or be sealed therein at its outer surface. In such a case, a branch connection can be made to the cavity 24 to allow biaxial flow to or from the cavity and the passage created between the needle 74 and conduit 20. This causes the needle 74 after initial penetration, to remain in place and serve as one of the biaxial flow paths.

As can be appreciated, other coaxial conformations can be derived from the foregoing to effectuate biaxial flow.

The foregoing specification teaches the broad utilization of coaxial members for biaxial flow and the insertion thereof with the attendant process therefor. As a consequence, the following claims should be the sole parameter in defining the scope and spirit of the biaxial flow device and process, and should be read in their broadest scope and spirit.

I claim:

1. An apparatus for simultaneously withdrawing and implacing fluid within a blood vessel comprising:

an insertion conduit suitable for extending into a blood vessel;

a hub connected to said insertion conduit having means to connect said insertion conduit to a device for withdrawing fluid from a blood vessel;

one-way valve means in fluid connected relationship to said insertion conduit to prevent the flow of fluid through said insertion conduit from said blood vessel;

a biaxial branch flow device having first and second branches and a main conduit within said device being in fluid communication with said insertion conduit through said hub;

said first branch within said biaxial flow device adapted for receiving fluid from said insertion conduit; and, a tube connected with said biaxial branch flow device for coaxially passing through said insertion conduit valve means and said main conduit in spaced relationship from the interior walls of said main conduit to allow fluid flow therebetween and wherein said tube is connected at one end to said second branch and extends at its other end to the end of or beyond the distal end of said insertion conduit.

2. The apparatus as claimed in claim 1 wherein:

said means to connect said insertion conduit comprises a syringe coupling on said hub.

3. The apparatus as claimed in claim 1 further comprising:

a cavity within said hub in flow connected relationship to said insertion conduit; and, said one-way valve means being within said cavity and adapted for receiving said tube after withdrawal of a needle.

4. The apparatus as claimed in claim 3 further comprising:

an elastomeric valve forming said valve means having a slit for the passage of said tube and needle therethrough.

5. The apparatus as claimed in claim 4 in combination with a needle having a connection adapted to being received in said hub and passing through and out of said insertion conduit for penetrating a blood vessel with said insertion conduit therearound.

6. The apparatus as claimed in claim 4 further comprising:

a needle adapted to be used through said insertion conduit having at least one chamfered sloping surface to provide an enlargement of an opening within a blood vessel punctured by said needle.

7. A biaxial flow device for withdrawing fluid from a blood vessel and simultaneously replacing fluid through a single opening therein comprising:

a hub member with an axial passage therethrough;

an insertion conduit extending from one end of said hub member adapted for placement within an opening of a blood vessel in connected relationship to and being in communication with said axial passage;

a valve member within the axial passage of said hub member configured to provide one way flow through said axial passage;

connection means in said hub adapted to receive a needle which can extend in coaxial relationship with and outwardly through said insertion conduit to cause a penetration of a blood vessel, and which needle can be later withdrawn;

a biaxial flow insert device for connection to said connection means and through said valve member as a replacement for said needle and having a main conduit and a tubular member;

said main conduit being in communication with said insertion conduit and having a passage connected thereto as a branch for outward flow therefrom; and, said tubular member being coaxially implaced in said main conduit in spaced relationship from the inner surface thereof to allow flow therebetween and being connected to a second branch for conducting fluid therethrough and said tubular member extending to or beyond the distal end of said insertion conduit so that fluid can pass simultaneously in and out of a blood vessel through the respective insertion conduit and tubular member.

8. The apparatus as claimed in claim 7 further comprising:

means to connect tubes to the respective branches of said biaxial flow device.

9. The apparatus as claimed in claim 8 further comprising:

a ledge within the axial passage of said hub against which said main conduit of said biaxial flow device is seated to provide a substantially uniform interior surface so that the lumen created thereby will not substantially distort laminar flow of blood therethrough.

10. The apparatus as claimed in claim 7 further comprising:

a valve configured of an elastomeric material and having a slit therethrough which is in the closed position until said tubular member of said biaxial flow device passes therethrough; and, means for securing said valve within the axial passageway.

* * * * *